United States Patent [19]

Cornwell

[11] 4,178,918

[45] Dec. 18, 1979

[54] AUTOMATIC BLOOD PRESSURE MEASURING AND RECORDING SYSTEM

[76] Inventor: Lionel B. Cornwell, 52 Madison Springs Dr., Madison, Conn. 06443

[21] Appl. No.: 833,608

[22] Filed: Sep. 15, 1977

[51] Int. Cl.² ............................................... A61B 5/02
[52] U.S. Cl. ..................................... 128/682; 128/688
[58] Field of Search .................... 128/2.05 M, 2.05 A, 128/2.05 C, 2.05 E, 2.05 G, 2.05 N, 2.05 Q, 2.08

[56] References Cited

U.S. PATENT DOCUMENTS

| | | | |
|---|---|---|---|
| 3,146,777 | 9/1964 | Lee | 128/2.05 A |
| 3,480,004 | 11/1969 | Edwards | 128/2.05 M |
| 3,572,320 | 3/1971 | Gerold et al. | 128/2.05 G |
| 3,811,439 | 5/1974 | Brown | 128/2.05 M |
| 3,814,083 | 6/1974 | Fletcher | 128/2.05 A |
| 3,905,353 | 9/1975 | Lichowsky | 128/2.05 G |
| 3,915,156 | 10/1975 | Wastl et al. | 128/2.05 E X |
| 3,951,137 | 4/1976 | Conkle et al. | 128/2.08 |
| 4,058,117 | 11/1977 | Kaspari et al. | 128/2.05 A |
| 4,069,815 | 1/1978 | Lee | 128/2.05 A |

OTHER PUBLICATIONS

Gomberg et al., "Device . . . Measurement of Blood Pressure", Biomed. Eng., Mar.-Apr. 1976, vol. 10, No. 2, pp. 70-73.

*Primary Examiner*—Lee S. Cohen
*Attorney, Agent, or Firm*—Alphonse R. Noë; Joseph B. Lazaroff

[57] ABSTRACT

A noninvasive blood pressure measuring and recording system includes an inflatable cuff for encircling a portion of the human body, a pump for inflating and deflating the cuff for selectively occluding an arterial vessel, a detector for detecting flow variation through the arterial vessel as cuff pressure is decreased, and a recorder for recording cuff pressure values corresponding to the detected flow variation. The pump is a reversible single stroke sleeve diaphragm pump pneumatically coupled to the cuff and provides a selected, repeatable linear rate of pressure change for accurate, repeatable measurements through an automatically controllable motor operating at a selected constant speed to actuate the pump. A speed control changes the linear rate of pressure change in response to detected flow variations to enhance accuracy of measurement of selected variations, such as those identified with the systolic and diastolic pressures. A variable volume ballast tank may be pneumatically coupled to the cuff and pump to accommodate different cuff sizes. Pressure and flow variation signals may be utilized to simply and easily provide one or more different representations or measurements of detected flow variations, including additional aural representation concurrent with the measurement process for aural diagnosis.

10 Claims, 8 Drawing Figures

Fig. 8.

AUTOMATIC BLOOD PRESSURE MEASURING AND RECORDING SYSTEM

BACKGROUND OF THE INVENTION

1. Field of the invention

This invention relates to an automatically operated non-invasive blood pressure measuring and recording system, and more particularly to a system of the type which includes an inflatable cuff for encircling a portion of the human body, usually the arm, means for inflating and deflation the cuff for selectively occluding an arterial vessel, means such as a microphone for detecting flow variations through the vessel as the cuff is delfated, e.g., those variations giving rise to Korotkov sounds identified with the systolic and diastolic pressures, and means for recording arm cuff pressure values in correspondence with the detected flow variations to provide a measurement record.

2. Description of the prior art

In known blood pressure systems the inflation of the pressure cuff is obtained by the operation of either a hand operated pump or an electric pump which is turned off when the desired pressure is reached. Deflation is accomplished with an air escape valve controlled either manually or with a servomechanism, as disclosed in U.S. Pat. No. 3,905,353, to provide a more or less constant rate of pressure drop. These known techniques have not been fully satisfactory, as they either are substantially nonlinear or require complicated means to approach linearity, and as they are affected by ambient conditions and do not provide the reproducability of pressure drop necessary for accurate, repeatable measurements. In addition, such techniques are not readily adaptable to provide a slower linear rate of pressure drop in the particular regions where systolic and diastolic pressures are detected, as suggested for improved measurement accuracy in U.S. Pat. No. 3,814,083 (col. 3, 1. 28-40). Finally, such inflation and deflation techniques do not lend themselves easily to automatic control over a full inflation and deflation cycle, which is desirable from the standpoints of reproducability of measurement and ease of operation.

In addition, known blood pressure systems provide a limited amount of measurement and diagnostic information, either in the form of chart traces of flow variations to be interpreted visually (e.g., U.S. Pat. Nos. 3,811,439, 3,867,926 and 3,878,834), in the form of readouts, either digital or analog, of systolic and diastolic pressures (e.g., U.S. Pat. Nos. 3,085,567, 3,396,405, 3,905,354, 3,623,476 and 3,500,822), or in the form of aural signals to be interpreted traditionally by a physician for the onset and disappearance of Korotkov sounds. Known systems heretofore have not provided multiple sources of information simply and easily, and have not included any arrangement permitting a diagnosis of the action of the artery,e.g., for detection of murmurs and the like, in connection with the blood pressure measurement.

Finally, known automatic blood pressure systems seeking to provide a high degree of automation have been complicated and expensive, and accordingly have failed to realize the potential economies of use by inexperienced or untrained operators.

SUMMARY OF THE INVENTION

A principal object of the present invention is to provide an improved automatic blood pressure measuring and recording system of the inflatable cuff type which is more suitable for clinical use. A further object of the invention is to provide such a system with an improved cuff inflation and deflating means which is capable of providing a linear, repeatable rate of pressure decrease for accurate measurement, which is adapted to be easily and automatically controlled, and which permits use with a variety of different cuff sizes. Still other objects of the invention are to provide such a system which is capable of generating a variety of measurement and diagnostic information, which is relatively simple and inexpensive to construct, and which is easy to use even by unskilled operators.

In a preferred embodiment of the invention to be described hereinbelow in detail, the blood pressure measuring and recording system includes improved means for inflating and deflation a cuff in the form of a reversible single stroke sleeve diaphragm pump defining a contained air space variable in volume. A motor, operating at a selected constant speed, drives a piston in the pump to linearly vary the volume of the contained air space and thereby linearly vary the pressure in the cuff. Motor speed control means, responsive to a manual start switch and limit switches on the pump, automatically operate the motor to inflate and deflate the cuff in a linear, reproducable manner. Preferably, the motor speed control means is further responsive to detected flow signals to change the pump motor speed to a lower constant rate in selected pressure regions to enhance accuracy of measurement.

In another aspect of the invention, an adjustable ballast tank is pneumatically coupled to the cuff and pump to accommodate different cuff volumes while permitting a small and economical pump to accomplish desired pressure changes.

In a further aspect of the invention, blood pressure measurements are recorded by a recording mechanism having a linear pneumatic actuator which receives the linearly varying cuff pressure to move a member carrying a recording pen and pen driver over a calibrated chart, and at the same time, to vary an electrical element, such as a resistance, to provide an electrical signal varying with cuff pressure. A detector, such as a microphone, provides a signal varying with the flow through the arterial vessel, and the detected signal is applied to the pen driver to provide a continuous trace on the calibrated chart as cuff pressure is decreased.

At the same time, the detected signal is applied to a signal analyzer arranged to provide outputs at the systolic and diastolic pressures, and the analyzer output signals are applied to the pen driver, to record the systolic and diastolic pressures on the calibrated chart. In addition, the detected signal is applied to an audio circuit to provide a high fidelity representation of arterial flow for diagnosis of specific kinds of arterial flow variations due to heart murmurs and the like, while a measurement is in progress. If desired, the electrical signal varying with cuff pressure and the analyzer output signals may be correlated in an auxiliary display, e.g., a digital display, to indicate the numerical values of the systolic and diastolic pressures. Thus temporary records on the display, permanent records on a calibrated chart, and an aural diagnostic signal all may be obtained as desired using the same equipment.

Other objects, aspects and advantages of the invention will be pointed out in, or be apparent from, the detailed description hereinbelow, considered together with the following drawings.

DESCRIPTION OF THE PREFERRED EMBODIMENT

Figure 1:
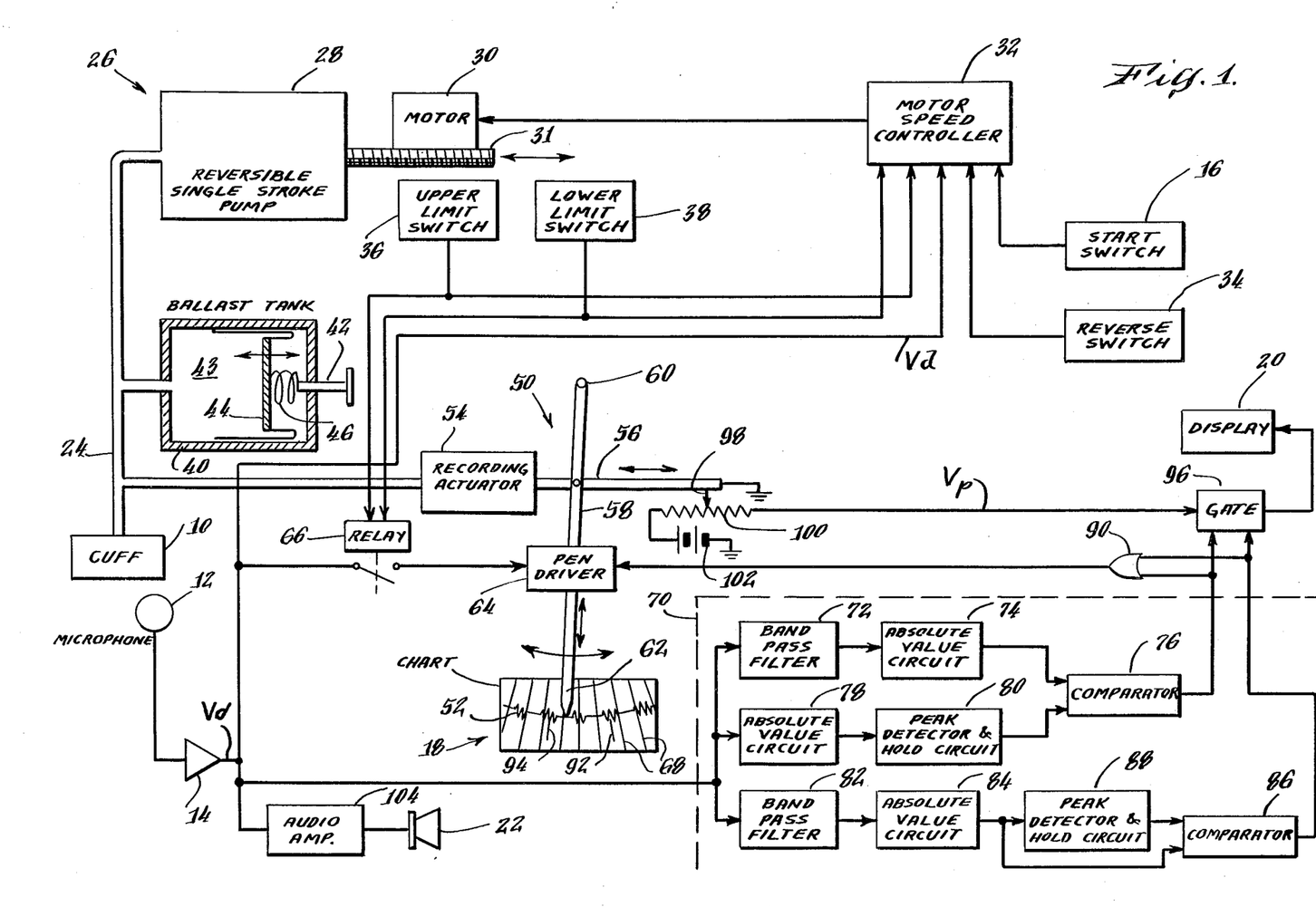
FIG. 1 is an essentially diagrammatic view of a blood pressure measuring and recording system constructed according to the present invention.

Referring to the drawings, FIG. 1 illustrates in diagrammatic form an automatic blood pressure measuring and recording system constructed in accordance with the present invention. The individual whose blood pressure measurement is to be taken is noninvasively coupled to the system through an inflatable cuff 10 and a microphone 12. The inflatable cuff 10 fastens around the individual's arm and, upon inflation and deflation, selectively occludes a brachial artery for measurement of the blood pressure therein. Adjacent the cuff 10, or mounted thereon, the microphone 12 detects sounds from the selectively occluded artery arising from flow variations therein and generates an output, amplified by an amplifier 14, to provide an electrical detection signal Vd. In the manner described below, after the cuff 10 and microphone 12 are in place, and a start switch 16 is closed, the system automatically performs a blood pressure measurement process correlating the cuff pressure with the detection signal to yield measurement records on a calibrated chart 18, a display 20, or both. At the same time, an aural representation of the flow variations is provided on a loudspeaker 22 for detection of particular variations arising from heart murmurs and the like.

As shown in FIG. 1, the cuff 10 is pneumatically coupled by means of a suitable conduit 24 to a pressure source 26 which, in accordance with the present invention, inflates and deflates the cuff over a pressure range providing the desired arterial occlusion. The pressure source 26, to be described below in greater detail with reference to FIGS. 2-4, comprises a fixed volume single stroke reversible piston pump 28 and an electric motor 30 operating at a selected constant speed for advancing and retracting the piston drive shaft 31 at a selected linear rate to cause a linear pressure increase and decrease in cuff 10. The speed of motor 30 is under the control of a speed controller circuit 32, to be described below in greater detail with reference to FIG. 8.

Briefly, the speed controller 32 has an input from start switch 16 to cause motor 30 to start a forward (inflating) stroke of drive shaft 31. An input from a manual reverse switch 34 is provided to reverse motor 30 to permit the measurement process to be aborted at any time during the measurement if desired. When the forward stroke of pump 28 is completed, and full inflation of cuff 10 is achieved, an upper limit switch 36 is tripped automatically by pump 28 to cause the controller 32 to reverse motor 30 and begin the reverse (deflating) stroke of piston drive shaft 31 during which measurements are taken.

As pressure in cuff 10 decreases, flow through the brachial artery will commence and a detection signal Vd will start to appear. At the commencement of the detection signal Vd, an input of this signal to controller 32 causes motor 30 to operate at a slower constant speed to enhance measurement accuracy in the regions of systolic and diastolic pressures, as suggested in U.S. Pat. No. 3,814,083. When the reverse stroke of pump 28 is complete, after measurements have been taken and recorded, the drive shaft 31 of pump 28 automatically trips a lower limit switch 38 to cause controller 32 to stop motor 30. As can be seen from the foregoing description of operation, the blood pressure measurement system of the present invention provides automatic cycling through the full measurement process in a simple manner using easily generated inputs to a controller which is required to change only the speed and direction of an electric motor to obtain the desired control.

As illustrated in FIG. 1, the cuff 10 and pressure source 26 are pneumatically coupled by means of conduit 24 to a ballast tank 40. Due to variatons in the circumferences of patient's arms, a convenional cuff of fixed dimensions is incapable of covering all arm circumferences. Six sizes of cuffs typically are required to accommodate all arm sizes, and each cuff requires a different volume of air in order to reach the required pressure for the underlying brachial artery to be occluded. To retain a constant air volume with all six cuffs and a single fixed volume pump 28, ballast tank 40 is provided. By varying the position of a manual control shaft 42, the internal volume 43 of ballast tank 40 is adjusted to complement the volume of a particular cuff 10 and to thereby obtain a constant volume for pump 28 to inflate. As shown in FIG. 1, the ballast tank 40 includes a diaphragm 44 coupled to control shaft 42 through a spring 46. By varying the control shaft 42, spring pressure is brought to bear on diaphragm 44 to adjust the internal volume 43 of the tank. Preferably, for ease of adjustment, the control shaft 42 is arranged with a plurality of settings each corresponding to a particular cuff size.

Figure 5:
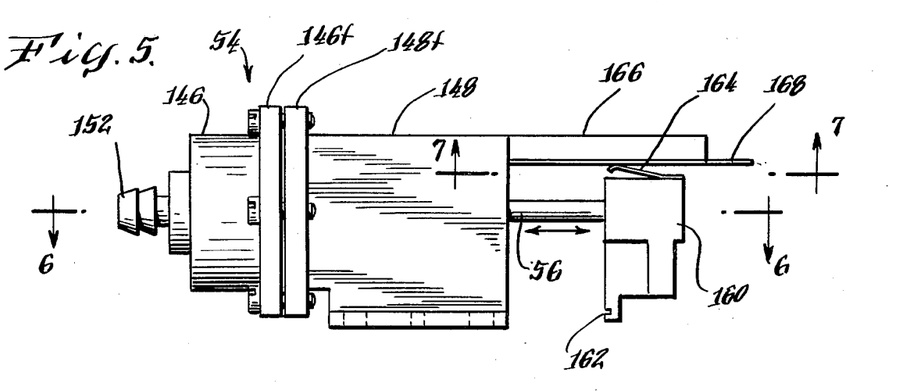
FIGS. 5-7 are views of the pneumatic recording actuator shown in FIG. 1, FIG. 5 being a side elevation, FIG. 6 a section on line 6—6 of FIG. 5, and FIG. 7 a partial section on line 7—7 of FIG. 5.
Figure 6:
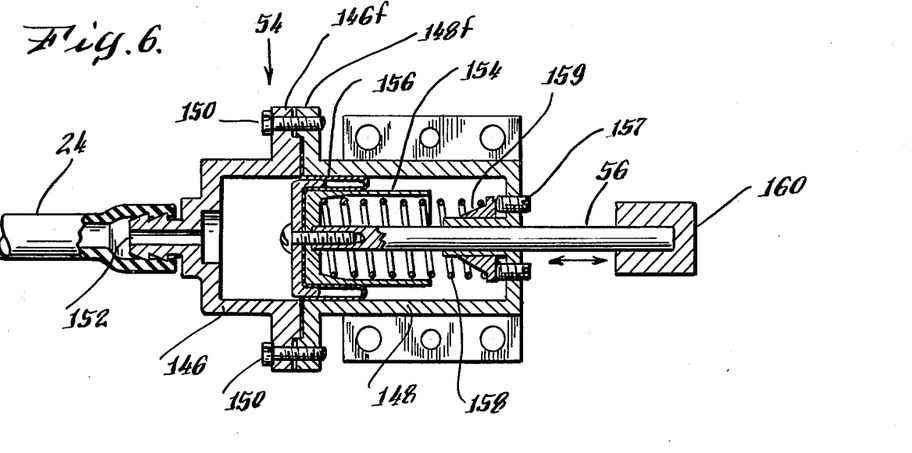
Figure 7:
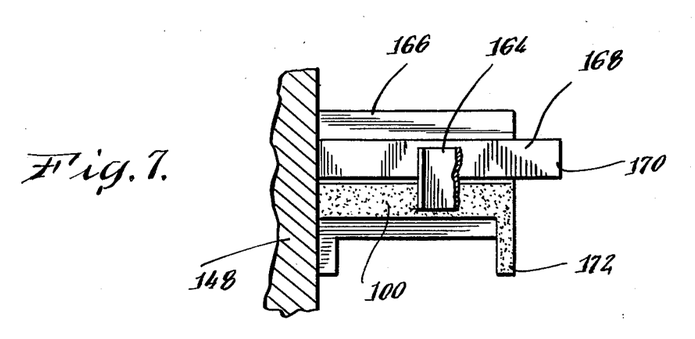

The linearly varying pressure in cuff 10 is applied, in conjunction with detection signal Vd, to a recording apparatus 50 arranged to generate an oscillatory record 52 of the detected arterial flow variations on calibrated chart 18. As illustrated in FIG. 1, cuff 10 is pneumatically coupled by conduit 24 to a pneumatic recording actuator 54 which, as will be described in greater detail below with reference to FIGS. 5-7, is arranged to translate the cuff pressure into a corresponding lengthwise mechanical displacement of an output shaft 56. An arm 58, pivoted at 60, is linked to shaft 56 and rotated thereby. The arm 58 mounts a radially movable recording pen 62 above chart 18. A dynamic pen driver 64, carried by arm 58, receives the detection signal Vd through the contacts of a relay circuit 66 and drives the recording pen 62 in a radial direction in proportion to the detection signal.

The recording apparatus 50 operates in the following manner: As pump 28 inflates cuff 10, arm 58 swings the pen 62 across chart 18. Because no record is to be made during inflation of the cuff, relay circuit 66 is arranged to have its contacts open during this time to prevent a signal from being applied to pen driver 64. When the upper limit switch 36 is actuated to reverse the pump motor 30, the contacts of relay circuits 66 are closed in response thereto.

As pump 28 linearly deflates cuff 10, arm 58 pivots steadily across chart 18. Calibration lines 68 on chart 18 indicate in appropriate units (e.g., mm. Hg) the cuff pressures corresponding to the various positions of arm 58 thereover. As detection signals Vd are received through the closed contacts of relay circuit 66, pen driver 64 responds by moving recording pen 62 radially back and forth to provide an oscillating trace 52 of the detected flow variations in a permanent form on chart 18. Through the use of calibration lines 68, the chart 18 will show at what cuff pressures the various arterial flow variations have taken place. When cuff 10 is fully deflated and pump 28 actuates the lower limit switch 38, the contacts of relay circuit 66 are again opened in preparation for a subsequent cycle of operation.

In addition to the record of arterial flow variation versus cuff pressure provided on chart 18, the blood pressure measuring system of the present invention is arranged to provide an accurate measurement and record of the systolic and diastolic pressures of the arterial vessel. A precise indication of the systolic and diastolic pressues is provided by a signal analyzer 70 receiving the detection signal Vd and preferably having the circuit arrangement described in U.S. Pat. No. 3,814,083, incorporated herein by reference.

Briefly, such a signal analyzer 70 operates by processing detected Korotkov sounds and utilizes a microphone 12 having a flat frequency response over the range of 10-100 Hz. The amplified microphone output Vd is supplied to a systolic Korotkov sound detecting system comprised to two channels. One channel of the system has a bandpass filter 72 having a range from 18 to 26 Hz. These signals in the bandpass range are passed to an absolute value circuit 74 which provides output signals representative of the absolute values of the filtered input signal. The signals from the absolute value circuit 74 are passed to a comparison circuit or comparator 76.

The other channel of the systolic Korotkov sound detecting system includes an absolute value circuit 78 which provides absolute value signals to a circuit 80 which detects peak values and holds the maximum peak value detected. The output of the peak detector 80 is also supplied to the comparison circuit 76. The comparison circuit is constructed and arranged to consider the output of circuit 74 as a numerator value and the output of circuit 80 as a denominator and produce an output signal dependent on the ratio value of the two input values. The comparison circuit is further arranged to produce a positive voltage output signal only when the ratio value is equal to or greater than 0.45. The comparator may be a standard commercial item such at the National Semiconductor LM 311 which is conventionally used as an amplifier with two operational states. Whenever the ratio is less than 0.45, the amplifier output is negative or zero; otherwise it saturates at full scale positive.

The processor circuitry also includes a channel for diastolic Korotkov sound detection. This channel includes a bandpass filter 82 having a frequency range from 40 to 60 Hz. The output of the filter 82 is supplied to an absolute value circuit 84 which provides absolute value output signals. The signals from circuit 84 are supplied directly to a comparison circuit or comparator 86 and to a circuit 88 which detects peak values and holds the maximum peak value detected. The output of the peak detector 88 is supplied to the comparison circuit 86. Comparison circuit 86 receives the detector output 88 as a denominator value and the absolute value signal as a numerator and provided an output signal when the ratio value falls below a value of 0.17.

The output signals from comparator 76 and comparator 86 are supplied to an OR gate 90, the output of which will be signals occurring at the systolic and diastolic events. The systolic and diastolic signals are applied to pen driver 64 in recording apparatus 50, preferably at a higher signal level than the detection signal Vd, so as to provide higher amplitude traces 92, 94 on chart 18 which are distinguishable form the flow variation trace 52. Thus there is automatically and permanently provided on chart 18 both a continuous record of arterial flow variations versus pressure and an accurate record of detected systolic and diastolic pressures.

The systolic and diastolic pressures also may be recorded temporarily if desired on the display 20, which preferably is of the digital variety showing the detected values in alphanumeric characters. To obtain such a display, the systolic and diastolic signals from analyzer 70 may be supplied to control the operation of a gate circuit 96. When the gate circuit 96 receives either the systolic or diastolic signals, the gate circuit is arranged to pass along to display 20 a pressure signal Vp which is proportional to cuff pressure values for the time that the gate is operated. In accordance with the present invention, the cuff pressure signal Vp is automatically generated by the operation of pneumatic recording actuator 54. As shown in FIG. 1, the output shaft 56 of actuator 54, which is displaced linearly in relation to cuff pressure, carries a contact element 98 which varies the characteristics of an electrical device such as a resistance 100. The pressure signal Vp may be derived from the varying resistance 100, e.g., by means of the illustrated voltage divider arrangement employing a voltage source 102 in series with the resistance 100.

Still another form of useful diagnostic information may be provided by the blood pressure system of the present invention. By using a microphone 12 with a wide frequency response, such as from 5 to 5000 Hz., and a wideband audio amplifier circuit 104, the loudspeaker 22 will provide not only the fundamental wave or pulse, but also all harmonics and overtones, making it possible to hear a murmur and the tone character of the murmur. Such a high fidelity representation of arterial flow variations in aural form is useful for diagnostic purposes and is readily provided in the present system as a concomitant to the previously described measurement and recording functions.

The blood pressure measuring system of the present invention thus provides a versatile array of useful records and information on chart 18, display 20, and loudspeaker 22. If desired, various switches (not shown) may be provided to obtain such records and information either independently or simultaneously.

Figure 2:
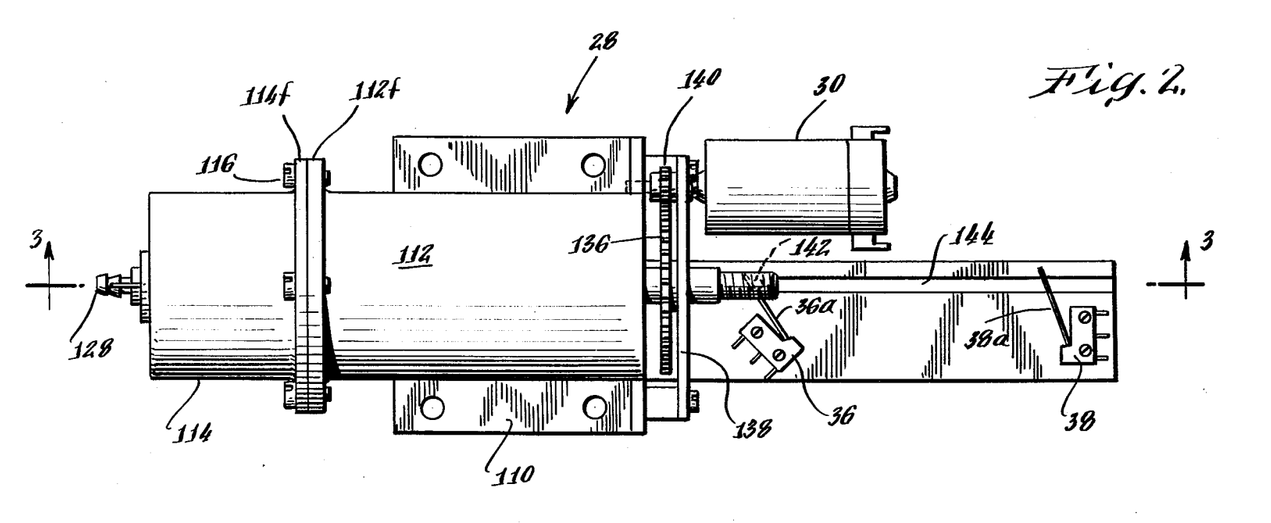
FIGS. 2-4 are views of the inflating and deflating means shown in FIG. 1, FIG. 2 being a plan view, FIG. 3 a section on line 3—3 of FIG. 2, and FIG. 4 an end elevation with portions shown in phantom for clarity.
Figure 3:
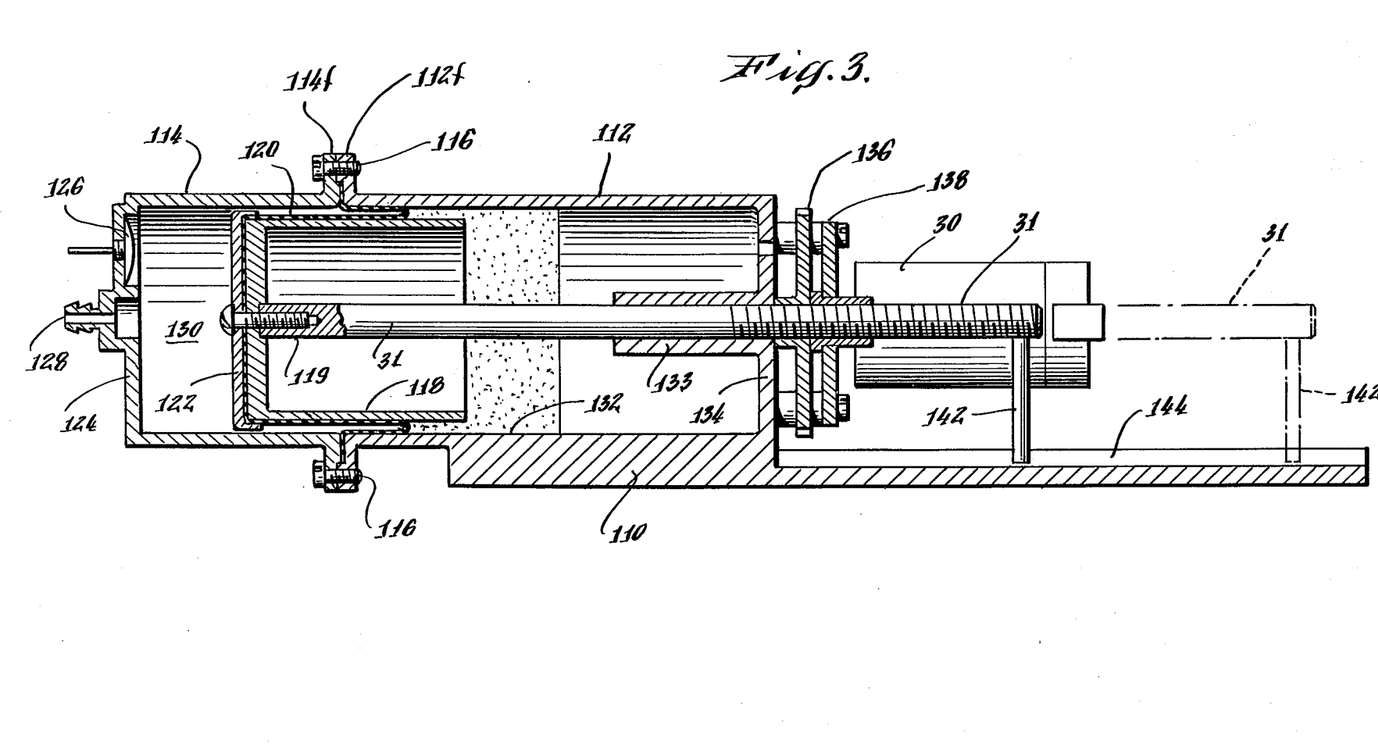
Figure 4:
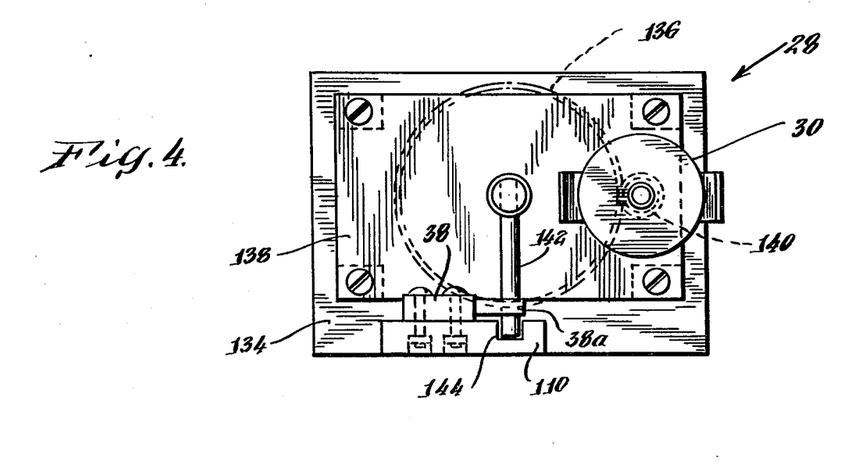

Turning again to pressure source 26, FIGS. 2-4 illustrate in detail a preferred embodiment of the construction thereof. Pump 28 comprises a base 110 mounting an integral cylindrical housing portion 112 having a flange 112f joined to the flange 114f of a second cylindrical housing portion 114 by fasteners 116. Within the cylindrical inner space formed by mating housing portions 112, 114 is a piston 118 secured to drive shaft 31 by fastener 119. The piston 118 is coupled to cylinder portions 112, 114 by a foldable cylindrical sleeve membrane or diaphragm 120, made for example of rubber, and attached to one end to piston 118 by means of a retainer plate 122 and fastener 119, and attached at the other end between housing flanges 112f, 114f. An end wall 124 of cylindrical housing portion 114 contains an umbrella relief valve 126 and an outlet connector 128 joining to conduit 24. The end wall 124, housing portion 114, and diaphragm 120 form a contained interior chamber or air space 130 in pump 28 which is variable in volum by movement of piston 118 to cause the inflation and deflation of cuff 10. The diaphragm 120 folds over itself as the piston 118 moves and thereby maintains a leakage free seal between piston 118 and cylindrical housing 112, 114 for reliable, repeatable pressure changes.

When the cuff is fully deflated, and piston 118 is near the right end (as seen in FIG. 3) of the housing, the pressure in the contained space 130 is essentially the ambient pressure and there is no pressure loading of diaphragm 120. Without any loading, the folded diaphragm 120 tends to slip along the interior surface of the housing as the piston starts its forward stroke (toward the left in FIG. 3), which may result in jamming of the diaphragm or nonlinear pressure changes if subsequent loading causes the diaphragm to slip back. To avoid such undesired slippage when starting the pump on its forward stroke, the interior surface of housing portion 112 is provided with a frictional lining 132 to grip the diaphragm 120. The frictional lining preferably is formed with an abrasive, as provided for example by sandpaper grit, or is formed with a tacky substance.

As shown in FIG. 3, the piston drive shaft 31 is journalled through a hub 133 in end wall 134 of housing portion 112 and is threaded. A gear 136 threadably engages shaft 31 and is fixed against axial travel by end wall 134 and a retaining plate 138. The gear 136 is rotated by a meshing pinion 140 rotatably driven by pump motor 30 to thereby move drive shaft 31 axially in a forward, inflating stroke or in a reverse, deflating stroke as required by controller 32. From the foregoing description it can be seen that pump motor 30, when operated at a constant speed, will cause linear movement of piston 118 and a linear, positively controlled buildup or decrease of pressure in cuff 10. As it is a simple matter to operate motor 30 at a constant preselected speed, the pressure source 26 of the present invention provides a simple and uncomplicated device for achieving linear and repeatable rates of pressure decrease in cuff 10 for accurate blood pressure measurements.

As illustrated in FIGS. 2–4, the piston drive shaft 31 carries near its end a transverse pin 142 which rides in a slot 144 in base 110 to prevent rotation of shaft 31. In addition, as it travels lengthwise with shaft 31, the pin 142 is arranged to trip actuators 36a and 38a of the upper and lower limit switches 36 and 38, mounted on base 110 in positions corresponding to the maximum forward and reverse positions of piston 118. Accordingly, the pump 28 is readily and easily adapted to provide signals at the maximum and minimum cuff pressures for automatic control of the pump through motor speed controller 32.

The construction of pressure source 26 is such that base 110, housing portions 112, 114 and piston 118 may be made of injection molded plastic, for economical construction.

FIGS. 5–7 illustrate in greater detail the construction of the preferred embodiment of the recording actuator 54 of FIG. 1. As shown in FIGS. 5–7, the actuator 54 comprisescylindrical mating housing portions 146, 148 having flanges 146f, 148f joined by fasteners 150. An inlet connector 152 admits pressurized air from cuff 10 through conduit 24 to a contained space formed by a piston 154, a foldable sleeve diaphragm 156, and housing portion 146. Changing pressure in the space moves piston 154 against the resistance of a spring 158 to displace actuator shaft 56, joined to piston 154, in an axial direction. By making the resistance of spring 158 proportional to pressure, displacement of actuator shaft 56 will be linearly related to the pressure in cuff 10. Adjustment screws 157 bearing on spring retainer 159 permit adjustment of the position of shaft 56 and calibration of recording apparatus 50.

Secured to actuator shaft 56 is a member 160 providing a coupler 162 for attachment to the pivotable recording arm 58. Member 160 also carries a wiper 164 functioning as the electrical contact 98 of FIG. 1. A platform 166 on housing portion 148 carries resistance strip 100 in contact with the wiper 164, and a parallel conductive jumper strip 168 also is in contact with wiper 164 so as to present at output terminals 170, 172 (FIG. 7) a resistance which varies linearly with the displacement of actuator shaft 56 and thus linearly with the pressure in cuff 10.

Figure 8:
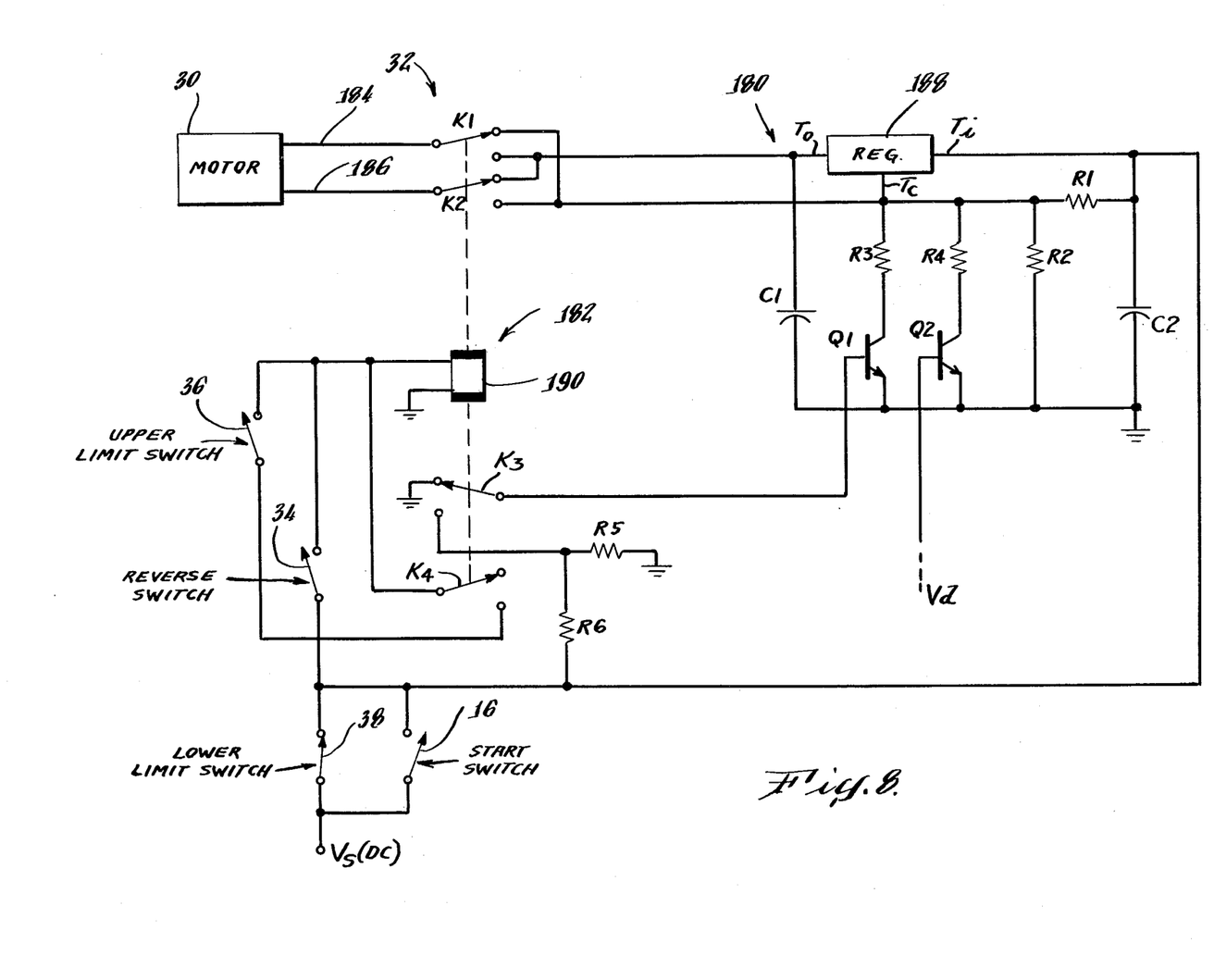
FIG. 8 is a schematic diagram of the speed control means shown in FIG. 1.

FIG. 8 illustrates in greater detail the construction of pump motor speed controller 32 of FIG. 1. As shown in FIG. 8, controller 32 comprises a regulator circuit 180 and a relay circuit 182 connected to pump motor 30, to switches 16, 34, 36 and 38, and to a line carrying the detection signal Vd. The motor 30 is a DC voltage sensitive type which produces at its terminals 184, 186 a counter EMF in direct ratio to its rotational speed (R.P.M.), and which thus is controllable by regulating its input power to obtain a prescribed counter EMF.

Regulation of the speed of motor 30 is provided by regulator circuit 180, which comprises a regulator 188, for example a model LM-117 made by National Corporation, having a power input terminal Ti, a power output terminal To, and a control terminal Tc to which a control voltage is applied. In conventional regulator fashion, the regulator 188 has terminals To and Tc connected to motor terminals 184, 186 and adjusts the power supplied to the motor 30 to maintain its counter EMF equal to the control voltage applied at regulator control terminal Tc.

The control voltage at terminal Tc, and thus the speed of pump motor 30, is set by a switchable voltage divider circuit comprising resistors R1 through R4 and transistor switches Q1 and Q2. Capacitors C1 and C2 are provided to damp switching transients. As shown in FIG. 8, the regulator circuit 180 permits the pump motor to be operated at different constant speeds by applying, at suitable times, different control voltages at regulator control terminal Tc. When a cycle of operation is started, transistor switches Q1 and Q2 are open, and closure of start switch 16 applies a source of voltage Vs to regulator input Ti and to the series circuit formed by resistors R1 and R2. The voltage across resistor R2 appears at regulator control terminal Tc and the regulator 188 establishes a corresponding rate of motor speed to provide the desired inflation rate in cuff 10. Upon actuation of the upper limit switch 36 (when the cuff 10 is fully inflated), relay circuit 182 causes transistor Q1 to conduct, thereby placing resistor R3 in parallel with resistor R2, lowering the control voltage at terminal Tc, and reducing the speed of motor 30 to a second constant rate. When microphone 12 produces a detection signal Vd, transistor Q2 is caused to become conductive, thereby placing resistor R4 in parallel with resistors R2 and R3, and further lowering the control voltage and motor speed to a third constant rate selected to provide increased accuracy of detection of systolic and diastolic rates. It will be apparent that proper selection of the values of resistors R1 through R4 will permit predetermined constant rates of inflation and deflation to be achieved.

Relay circuit 182 governs motor 30 and regulator circuit 180 through a cycle of operation by means of a relay 190 having contacts K1 through K4 illustrated in the state each assumes when the relay 190 is deenergized. As will be explained below from a description of the relay's control features, the relay 182 remains deenergized during the inflation stroke of pump 28, becomes energized in response to actuation of the upper limit switch 36, and remains energized during the deflation stroke.

Relay contacts K1 and K2, as shown in FIG. 8, are connected between motor 30 and regulator 188 to reverse the polarity of voltage applied to motor 30 at the end of the inflation stroke of the pump and to cause the motor to reverse its direction and perform the deflation stroke. Contact K3 is arranged to connect a voltage, derived for example from the voltage divider formed by resistors R5, R6 and voltage source Vs, to the base of transistor switch Q1 to cause it to conduct and thereby effect a change in motor speed. Contact K4 is provided to hold relay 190 energized during the deflation stroke.

Control of the motor speed controller 32 through a cycle of operation is effected by switches 16, 34, 36 and 38. The voltage source Vs is connected to regulator circuit 180 through a parallel connection of start switch 16 (closed manually) and lower limit switch 38 (which remains closed except at the end of a deflation cycle when it is opened by travel of the pump mechanism). The voltage source Vs also is connected to relay 190 through the lower limit switch 38 in series with a parallel connection of reverse switch 34 (closed manually), upper limit switch 38 (closed at the end of an inflation stroke), and relay contact K4 (closed upon energization of relay 190).

Accordingly, the operation of motor speed controller 32 through a cycle of operation may now be explained. At the beginning of a cycle, lower limit switch 38 is open. Momentary closure of pushbuttom type start switch 16 applies voltage source Vs to regulator circuit 180, which causes the pump motor 30 to start an inflation stroke, thereby closing lower limit switch 38 and holding the connection of voltage source Vs to the regulator circuit for the remainder of the cycle.

At the end of an inflation stroke, upper limit switch 36 automatically closes, thereby applying voltage source Vs to relay 190. The relay energizes, contacts K1 and K2 reverse motor 30, contact K3 causes transistor Q1 to conduct and changes motor speed, and contact K4 holds the relay energized throughout the remainder of the deflation stroke.

Alternatively, the deflation stroke may be initiated by momentary closure of pushbutton type reverse switch 34, which similarly energizes relay 190.

During the deflation stroke, detection signal Vd appears and changes the motor speed again to a value enhancing the accuracy of blood pressure measurements.

At the end of the deflation stroke, lower limit switch 38 opens, simultaneously disconnecting voltage source Vs from relay 190 and regulator circuit 180. Pump motor 30 stops, relay 190 energizes, and the circuit is placed in condition for the start of a new cycle.

From the foregoing description it can be appreciated that the blood pressure measuring and recording system of the present invention provides several major advantages. Accurate, linearly variable cuff pressures are easily provided for enhanced accuracy of measurement. Simple automatic control for the system also is provided. And versatile diagnostic outputs and records of measurements are easily generated. All these operational advantages are realized, moreover, in an apparatus which is more economical for the degreee of accuracy achieved than automatic devices heretofore known.

Although a specific embodiment of the invention has been disclosed herein detail, it is to be understood that this is for the purpose of illustrating the invention and should not be construed as necessarily limiting the scope of the invention since it is apparent that many changes can be made to the disclosed structures by those skilled in the art to suit particular applications.

I claim:

1. In a noninvasive blood pressure measuring and recording system of the type which includes an inflatable cuff forencircling a portion of the human body, means for inflating and deflating the cuff for selectively occluding an arterial vessel, means for detecting flow variations through the artery and means for recording the arm cuff pressure values corresponding to the detection of desired flow variations through the artery as cuff pressure is decreased, the improvement therein enabling reproducibility of cuff pressure decrease and controlled variability of constant rates of pressure decrease which comprises:

the means for inflating and deflating the cuff comprising a single stroke reversible pump having a piston, a cylinder and a flexible sleeve diaphragm, the piston being movable within the cylinder and joined thereto through the flexible sleeve diaphragm, the diaphragm being arranged to fit in a folded position between the cylinder and piston and to maintain a pressure seal therebetween, the piston, cylinder and diaphragm forming a variable volume, contained air chamber pneumatically coupled to the cuff, controllable motor means operable at a preselected constant speed for moving the piston within the cylinder to vary the volume of the contained air chamber in a predetermined fashion, thereby to produce a corresponding predetermined and precise pressure variation in the inflatable cuff for accurate blood pressure measurements, and control means for controlling the motor means during decrease of cuff pressure in response to the flow variation detection means to operate the motor means at a different preselected constant speed following initial detection of flow variations in the arterial vessel.

2. The improved noninvasive blood pressure measuring and recording system as claimed in claim 1 further comprising a variable volume ballast tank pneumatically coupled to the cuff and to the contained air chamber of the pump.

3. The improved noninvasive blood pressure measuring and recording system as claimed in claim1 wherein the control means for controlling the motor means includes a regulator circuit means for adjusting power supplied to the motor means, the flow variation detection means includes means for generating a signal and the regulator circuit means includes means to respond to the signal generated by the flow variation detection means to adjust the power supplied to the motor means.

4. The improved noninvasive blood pressure measuring and recording system as claimed in claim 3 wherein the control means further includes limit switch means comprising an upper limit switch actuated by the pump at a piston location corresponding to a fully inflated condition of the cuff, and wherein the control means responds to actuation of the upper limit switch by reversing the pump motor means to initiate deflation of the cuff, and a lower limit switch actuated by the pump at a piston location corresponding to a deflated condition of the cuff, and wherein the control means responds to actuation of the lower limit switch to turn off the pump motor means.

5. The improved noninvasive blood pressure measuring and recording system as claimed in claim 4 wherein the detection means comprises a microphone for generating the detection signal and wherein the recording means comprises a pen driver responsive to the detection signal, the detection signal being applied to the pen driver through the contacts of a relay circuit being responsive to the upper limit switch, said relay circuit closing said contacts upon actuation of the upper limit switch, and to the lower limit switch, said relay circuit opening said contacts upon actuation of the lower limit switch.

6. The improved noninvasive blood pressure measuring and recording system as claimed in claim 5 wherein the recording means further comprises a signal analyzer, the signal analyzer includes means responsive to the detection signal for generating signal outputs at the systolic and diastolic pressures of the arterial vessel, said systolic and diastolic signal outputs being applied to the pen driver for indication thereby of the systolic and diastolic events.

7. The improved noninvasive blood pressure measuring and recording system as claimed in claim 6 wherein the recording means further comprises a pneumatic actuator, an output member, the pneumatic actuator being pneumatically coupled to the cuff and arranged to displace the output member linearly in relation to cuff pressure, the pneumatic actuator including an operatively connected contact element moving with the output member for varying the characteristics of an electrical element to develop an electrical signal related to cuff pressure.

8. The improved noninvasive blood pressure measuring and recording system as claimed in claim 7 wherein the recording means comprises a chart recorder including a pivoted recording arm carrying a recording pen and said pen driver therefor, and wherein the actuator output member is coupled to the recording arm to pivot the arm in correspondence with cuff pressure.

9. The improved noninvasive blood pressure measuring and recording system as claimed in claim 4 wherein the detection means comprises a microphone for generating the detection signal and the recording means comprises, a signal analyzer, the signal analyzer including means responsive to the detection signal for generating signal outputs at the systolic and diastolic pressures of the arterial vessel, a chart recorder responsive to the detection signal, to the systolic and diastolic output signals from the analyzer, and to the cuff pressure, the chart recorder including a recording arm, a pneumatic actuator responsive to cuff pressure operatively connected to the recording arm for moving the recording arm and for moving a contact element operatively connected thereto to develop an electrical signal corresponding to cuff pressure, and display means responsive to the systolic and diastolic output signals from the analyzer and to the detection signal corresponding to cuff pressure for generating a display of the systolic and diastolic pressure of the arterial vessel.

10. The improved noninvasive blood pressure measuring and recording system as claimed in claim 9 further comprising an aural diagnosis means responsive to the detection signal and comprising loudspeaker means and a wide band audio circuit coupling the microphone to the loudspeaker means for providing an accurate aural representation of the arterial flow variations for diagnosis thereof.

* * * * *